United States Patent
Sambanthamurthi et al.

(10) Patent No.: US 9,381,145 B2
(45) Date of Patent: *Jul. 5, 2016

(54) BOTANICAL EXTRACTS FROM OIL PALM VEGETATION LIQUOR FOR COSMECEUTICAL APPLICATIONS

(71) Applicant: Malaysian Palm Oil Board, Kajang, Selangor (MY)

(72) Inventors: Ravigadevi Sambanthamurthi, Selangor Darul Ehsan (MY); Yew Ai Tan, Selangor Darul Ehsan (MY); Kalyana Sundram P. Manickam, Selangor Darul Ehsan (MY); Mohd Basri Wahid, Selangor Darul Ehsan (MY)

(73) Assignee: MALAYSIAN PALM OIL BOARD, Kajang, Selangor (MY)

( * ) Notice: Subject to any disclaimer, the term of this patent is extended or adjusted under 35 U.S.C. 154(b) by 0 days.

This patent is subject to a terminal disclaimer.

(21) Appl. No.: 14/513,068

(22) Filed: Oct. 13, 2014

(65) Prior Publication Data

US 2015/0196472 A1 Jul. 16, 2015
US 2016/0151259 A9 Jun. 2, 2016

Related U.S. Application Data

(63) Continuation of application No. 12/595,612, filed as application No. PCT/MY2008/000030 on Apr. 14, 2008, now Pat. No. 8,859,017.

(30) Foreign Application Priority Data

Apr. 12, 2007 (MY) .................. PI20070568

(51) Int. Cl.
| A61K 36/889 | (2006.01) |
|---|---|
| A61K 8/368 | (2006.01) |
| A61K 8/97 | (2006.01) |
| A61K 36/00 | (2006.01) |
| A61Q 5/00 | (2006.01) |
| A61Q 19/08 | (2006.01) |
| A61Q 19/10 | (2006.01) |
| A61Q 1/12 | (2006.01) |

(52) U.S. Cl.
CPC . *A61K 8/368* (2013.01); *A61K 8/97* (2013.01); *A61K 36/00* (2013.01); *A61K 36/889* (2013.01); *A61Q 5/00* (2013.01); *A61Q 19/08* (2013.01); *A61Q 19/10* (2013.01); *A61K 2800/10* (2013.01); *A61K 2800/522* (2013.01); *A61K 2800/92* (2013.01); *A61Q 1/12* (2013.01)

(58) Field of Classification Search
CPC .................................................. A61K 36/889
USPC .................................................. 424/727, 725
See application file for complete search history.

(56) References Cited

U.S. PATENT DOCUMENTS

| 4,232,122 A | 11/1980 | Zilliken |
| 7,101,563 B1 | 9/2006 | Vromen |
| 2003/0031740 A1 | 2/2003 | Sambanthamurthi et al. |
| 2008/0171029 A1 | 7/2008 | Lee |

FOREIGN PATENT DOCUMENTS

| CN | 1256912 A | 6/2000 |
| EP | 0 818 81 | 4/1987 |
| WO | WO-2005/118759 | 12/2005 |
| WO | WO-2006/090953 | 8/2006 |

OTHER PUBLICATIONS

Paolo U. Giacomoni, PhD, "Advancement in skin aging: the future cosmeceuticals", Clinics in Dermatology, (2008) 26, 364-366.*
Balasundram, et al., "Antioxidant properties of palm fruit extracts," Asia Pacific Journal of Clinical Nutrition,(2005), 4(4):319-324.
International Search Report for PCT Patent Application No. PCT/MY2008/000030.
Sundram et al, "Palm fruit chemistry and nutrition," Asia Pacific Journal of Clinical Nutrition, (2003), 12(3): 355-362.

* cited by examiner

Primary Examiner — Chris R Tate
Assistant Examiner — Deborah Davis
(74) Attorney, Agent, or Firm — Foley & Lardner LLP

(57) ABSTRACT

A cosmeceutical composition comprising phenolic compounds, fruit acids and sugars, extracted from the vegetation liquor of the palm oil milling process has been suggested. This composition is rich in antioxidants, and significantly improves skin health, including preventing aging of skin.

10 Claims, 2 Drawing Sheets

BOTANICAL EXTRACTS FROM OIL PALM VEGETATION LIQUOR FOR COSMECEUTICAL APPLICATIONS

CROSS-REFERENCE TO RELATED APPLICATIONS

This application is a Continuation Patent Application of U.S. Utility patent Ser. No. 12/595,612, filed Apr. 19, 2010, now U.S. Pat. No. 8,859,017, issued Oct. 14, 2014, which is the U.S. national stage application under 35 U.S.C. §371 of International Patent Application No. PCT/MY2008/000030, filed on Apr. 14, 2008, which claims priority to Malaysian Patent Application No. PI20070568, filed on Apr. 12, 2007, each of which is incorporated herein by reference in its entirety.

FIELD OF INVENTION

The present invention relates to cosmeceutical compositions having antioxidant properties and comprises compounds extracted from plant material. More particularly, the present invention relates to botanical extracts containing phenolic compounds, fruit acids and sugars from vegetation liquor of oil palm for skin health.

BACKGROUND OF INVENTION

The skin possesses the largest surface area in the body and serves as the protective layer for internal organs. It is a major target of oxidative stress and is designed to give both physical and biochemical protection and is equipped with a large number of defense mechanisms. The skin structure is quite complex comprising several layers, each of which plays a specific role and carries out different functions.

It is generally known that the deficiency of the appropriate skin care may lead to various skin problems, which may include accelerated skin aging, skin disorders and diseases. Relevant studies have reported that one of the primary contributors to such common skin problems is reactive oxygen species. Accordingly, high occurrence of potential biological components may cause oxidative damage of skin, as it is very susceptible to such reactions. It is also discovered that the aging of the skin occurs when collagen becomes hard and gets meshed with neighboring collagen fibers. As a result, the collagen is prevented from holding water and plumping up, which therefore gradually leads to reduced elasticity. Such condition may also lead to the skin becoming dehydrated and thus the underlying fat padding would disappear over a period of time.

Apart from the above, studies have also revealed that ultraviolet radiation exposure results in a number of changes in the skin including wrinkling, laxity, uneven pigmentation, brown spots, leathery appearance in addition to degradation of skin collagen and alteration of connective tissue.

With the loss of underlying support by fat padding and connective tissues, the skin begins to sag; it appears less supple and wrinkles form. Although wrinkles, fine lines and age spots are formed by the natural effects of getting older, one way to prevent them from appearing early on in life is to avoid direct sunlight.

Additionally, excessive exposure to sunlight also contributes to the production of free radicals. Basically, free radicals are created naturally during various metabolic processes in the cell whereby they are rendered inactive by antioxidants, as long as there are adequate amounts of antioxidants within our body to handle the free radicals produced in the body. However, there are circumstances where the body may not be able to produce enough antioxidants on its own to neutralize all the free radicals that are produced, resulting to cell damage and thus skin aging. Therefore the use of synthetic antioxidants and/or natural antioxidants as daily supplements is vital in this regard. Antioxidants can be obtained from our daily diet and in addition are often consumed as supplements.

Prior methods to prevent skin-aging included mixing of nutrient additive, anti-inflammation agent into cosmetic compounds. US20040241254 suggests cosmetic formulations containing Palm oil to treat age related skin problems. Many natural substances rich in antioxidants have been found to play a role in the prevention of skin aging. Also, the use of natural plant extracts having antioxidant properties instead of synthetic antioxidants is now gaining momentum.

According to the present invention, extracts derived from the vegetation liquor of oil palm have properties that promote skin health and slow down aging of the skin.

The major constituents in the oil palm vegetation liquor extract are phenolics, fruit acids, fruit sugars and glycerol. The said phenolic compounds possess antioxidant properties that help minimize damage caused by free radicals in the body resulting from metabolic processes or from environmental exposures. Skin elasticity decreases because of the action of elastase, an enzyme that decomposes elastin. The inhibition of elastase thus delays skin sagging. Collagen and hyaluronic acid also affect elasticity, moisture retaining property and softness of skin. Collagen which constitutes about 90% of dermis of skin is distributed all over the dermis to give appropriate elasticity and strength to the skin. Hyaluronic acid is widely distributed over the skin, ligament, and the like, and contributes in skin to cell adhesion, cell protection, formation of skin tissues, retention of tissue moisture, and maintenance of softness. Collagen and hyaluronic acid are decomposed in vivo by collagenase and hyaluronidase, respectively leading to moisture loss, wrinkles and sagging. Inhibition of collagenase and hyaluronidase would therefore also improve skin chemistry and delay aging of skin.

The said phenolic compounds in oil palm vegetation liquor extract significantly inhibit elastase activity. The vegetation liquor extract also possesses inhibitory action against collagenase and hyaluronidase activity. In addition the extract possesses anti-tyrosinase activity which is implicated in skin whitening.

It is therefore the primary object of the present invention to provide a composition based on phenolic compounds obtained from oil palm vegetation liquor, said composition contributes significantly in improving skin health and thus alleviating skin problems.

SUMMARY OF INVENTION

The present invention relates to a cosmeceutical composition comprising phenolic compounds extracted from vegetation liquor of the palm oil milling process where the composition improves skin health.

The present invention further relates to a method for treating or reducing the appearance of wrinkles and fine lines on the skin comprising applying to the skin an effective amount of biologically active phenolic and other compounds from the composition.

DETAILED DESCRIPTION OF THE INVENTION

Figure 1:
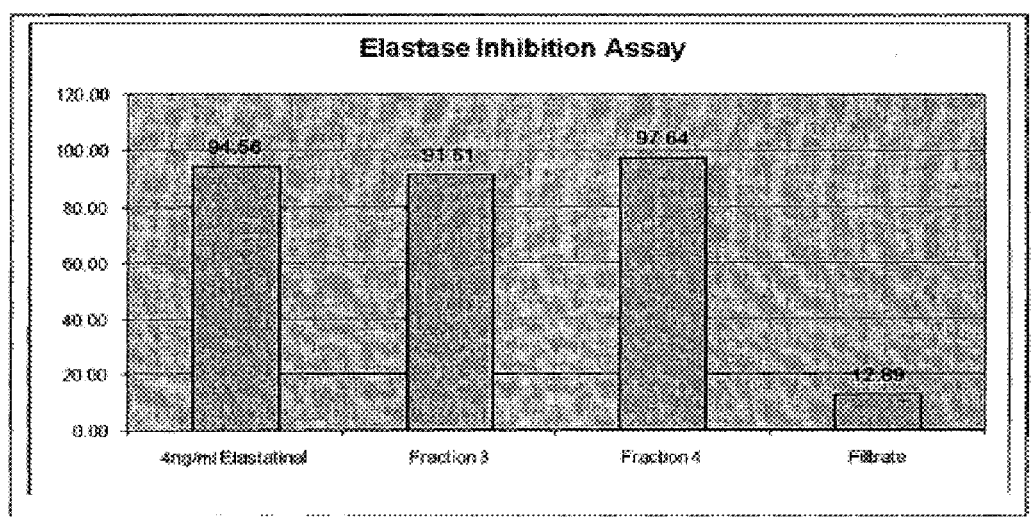
FIG. 1 is a bar graph of elastase activity measured spectrophotometrically.

The purpose of this invention is to present a botanical extract of oil palm vegetation liquor from the oil palm milling process for cosmeceutical applications to promote skin health and delay skin aging. Accordingly, the present invention also relates to an extraction process of antioxidants from the oil palm vegetation liquor from the milling process. The processing of oil palm produces large amounts of vegetation liquor rich in phenolic compounds, fruit acids, fruit sugars and glycerol which can be further enriched using membrane filtration technology as briefly disclosed in EP1398311.

The extract contains phenolic compounds, fruit acids, fruit sugars and glycerol which have a great integrated effect in inhibiting skin aging. The phenolics retard skin aging through several mechanisms including but not confined to elastase inhibition, collagenase inhibition, antioxidant activity, free radical scavenging, hyaluronidase inhibition and anti-inflammatory action. The anti-tyrosinase activity of the phenolic compounds promotes skin whitening. Inflammatory processes generate micro-scars that lead to blemishes and wrinkles Anti-inflammatory action of the oil palm phenolics can soothe, protect and heal skin tone and integrity. Antimicrobial activity of the palm phenolic extract plays a multiple role in preventing skin infection and improves the stability and thus shelf life of cosmeceutical formulations. Topical moisturisers are used to nourish and tone the skin and glycerol and sugars in the oil palm vegetation liquor extract support skin texture through hydration. Fruit acids have been used for improving skin texture through enhancement of epidermal exfoliation and similar acids are found in the oil palm vegetation liquor extract.

BEST MODE FOR CARRYING OUT THE INVENTION

The preparation of cosmeceutical formulations according to the present invention are described in detail by referring to the experimental examples. However, the present invention is not limited to these examples.

For the experimental examples, inventors isolated botanical extracts comprising phenolic compounds, fruit acids, fruit sugars and glycerol from oil palm vegetation liquor from the palm oil milling process and the prepared formulations containing these extracts (operation example) and composition without palm phenolic extract (comparison example).

The present invention focuses on cosmeceutical compositions comprising phenolic compounds which are potent antioxidants and prevent aging of the skin.

The present invention also describes cosmeceutical compositions containing synthetic materials like whitening and wrinkle elimination cosmetic substances to gain a synergistic combination of the natural compounds and the synthetic material.

The biologically active extracts of palm vegetation liquor useful in this invention can be prepared by any means capable of extracting phenolic compounds from the vegetation liquor using standard extraction techniques or techniques as disclosed briefly in U.S. Pat. No. 4,232,122, United States Application US 2003031740, and WO/2006/090953. Such extractions include but are not limited to ethanol, methanol, acetone, ethyl acetate and butanol.

In addition to direct use of an extract, it is also possible to use different fractions of the oil palm phenolic compounds. What constitutes an effective amount of an extract, or an active portion thereof, will depend on the purity of the extract. For example, if a crude phenolic-containing extract of about 10% purity is employed, the extract will normally be used at a concentration range of about 0.01-20% by weight of the composition. At a higher level of purity, a smaller percentage will be required to achieve the same effect. Assuming a substantially pure phenolic extract, i.e. an extract containing at least 80% active phenolics, the level will be about 0.01 to about 8% by weight of the composition.

The extract of substantially pure phenolics can be delivered in any form appropriate for topical application. Such forms include solutions, colloidal dispersions, oil-in-water or water-in-oil suspensions, creams, gels, lotions, gels, powders, foams, mousses, etc the methodology for formulation of different vehicle types is well known in the art and can be found in any standard cosmetic literature.

The extract of substantially pure phenolics can also be delivered in any form appropriate for oral intake. Such forms include liquids and powders.

The type of the cosmetics is not particularly limited, and may be, for example, personal care products such as skin creams, lotions, skin toners, face packs, and cleansing agents; make-up cosmetics such as lipsticks and foundation; or hair cosmetics. The cosmetics may be in any form without limitation. The skin preparation for external use may be, for example, ointment or various dermatological agents.

The compositions of the invention are useful in the prevention or treatment of any condition in which the activity of elastase or the reduction of elastin levels in the skin is a factor. For example, the compositions are useful for improving the firmness and elasticity of aging skin and for reducing the appearance of fine lines and wrinkles. The compositions can also be used for skin lightening. In addition, the compositions of the invention have a number of therapeutic uses. One example is the promotion of wound healing. The compositions can also be used in improving conditions such as scleroderma.

Content of Phenolic Compounds in Oil Palm

100 μl of palm extract were mixed with 0.2 ml Folin-Ciocalteau reagent (Sigma), 2 ml of $H_2O$, and one ml of 15% $Na_2CO_3$ and the absorbance was measured at 765 nm after 2 h incubation at room temperature. A standard curve was plotted with different concentrations of gallic acid and the total phenolic acid content expressed as gallic acid equivalent (GAE).

The following non-limiting examples illustrate the compositions and methods of the invention.

EXAMPLES unless otherwise specified, throughout the following examples, the oil palm phenolic extract employed is a crude solvent-free extract Anti-Elastase Activity Elastin is a scleroprotein in the connective tissue of skin that is largely responsible for skin elasticity. Elastin is broken down to soluble peptides and the dermis contents of this protein reduced during inflammatory and aging processes. The enzyme elastase is responsible for elastin degradation. Inhibition of elastase activity would therefore help maintain skin protein levels and elasticity. An assay to determine elastase inhibition by oil palm phenolic extract was thus carried out. Elastase activity was assessed spectrophotometrically by measuring the amount of the peptide 4-nitroanilide generated following the action of a pancreatic elastase on the substrate. N-Succinyl-Ala-Ala-Ala-p-Nitroanilide. N-Succinyl-Ala-Ala-Ala-p-Nitroanilide (Sigma) and the substances to be tested were pre-incubated at 37° C. and the reaction initiated by addition of the enzyme (Pancreatic Porcine Elastase, Roche). The amount of free 4-nitroanilide released was measured by determining the absorbance at 410 nm after 30 minutes. Buffer Tris-HCl 0.2M pH 8.0 was used as the negative control. Elastatinal at a final concentration of 20 ng/ml in the assay medium served as the positive control. The final concentration of oil palm extract in the assay medium ranged from 4% to 20% by volume amounting to 60 to 300 ppm gallic acid equivalent (GAE). The graph in FIG. 1 shows the results obtained. Maximum absorbance values were obtained for the negative control. Inhibition of elastase activity generated less 4-nitroanilide and consequently smaller absorbance values. Oil palm phenolics showed significant inhibitory action on elastase activity in a dose-dependent manner. The oil palm phenolic extract exhibited about 13% inhibitory effect while Fractions 3 and Fractions 4 representing fractions of the filtrate purified by flash chromatography exhibited about 92% and 98% inhibitory effect respectively. It was concluded that oil palm phenolics inhibit elastin degradation which would translate into beneficial effects on skin such as maintenance of elasticity and its consequent anti-aging effect Collagenase Inhibition Assay Collagenase (EC 3.4.24.3, 5 µg) was added to PZ-peptide (0.5 mg), a substrate of collagenase in 0.1 M Tris buffer (pH 7.4), with or without extract in a total volume of 1.7 ml. The mixture was incubated at 37° C. in a water bath for 30 min, and 1 ml of 25 mM citric acid solution was added to terminate the enzyme reactions. After mixing with 5 ml of ethyl acetate, the absorbance of the organic layer was measured by UV-spectrophotometry at 320 nm. Collagenase inhibition was calculated by following equation:

% Collagenase inhibition=[(Ac−As)/Ac]×100, where Ac was (the absorbance of control with collagenase−the absorbance of control without collagenase), and as was (the absorbance of sample with collagenase−the absorbance of sample without collagenase).

Oil palm extract exhibited significant collagenase inhibitory activity compared to the control.

Hyaluronidase (HAase) Inhibition Assay

HAase solution (7,900 units/ml in 0.1 M acetate buffer, pH 3.5) was mixed with 100 µl of sample and incubated at 37° C. in a water bath incubator for 20 min. The HAase activator (0.1 mL of 12.5 mM $CaCl_2$) was added and incubated further for 20 min. For the HAase reaction, 250 µl of hyaluronic acid (1.2 mg/ml), the substrate, in 0.1 M acetate buffer (pH 3.5) was added and incubated at 37° C. in a water bath incubator for 40 min. For termination of the HAase reaction, 0.1 ml of 0.4 N NaOH and 0.1 ml of 0.4 M potassium tetraborate were added and warmed in boiling water for 3 min. After cooling completely, 3 ml of DMAB reagent (4 g of r-demethylaminobenaldehyde, 350 ml of glacial acetic acid, and 50 ml of 10 M HCl) was added to the reactant and incubated at 37° C. in a water bath incubator for 20 min. HAase reaction product, 4-acetylglucosamine was measured by UV-spectrophotometry at 585 nm wavelength. HAase inhibition activity was expressed by the decrease compared to the control; % Hyaluronidase Inhibition=[(Ac−As)/Ac]×100, where Ac and As were the absorbance of control and sample, respectively. The control was 1% DMSO solution instead of extract.

Oil palm extract had significant HAase inhibitory activity.

Anti-Inflammatory Activity

Anti-inflammatory activity was measured according to manufacturer's instructions using the Cayman COX (ovine) Inhibitor Screening Assay Kit. (Catalog No. 560101) Using this kit, weak COX activity was observed.

Assay for Antioxidant Activity

Several methods were used to determine the antioxidant activity, two of which are described here.

Assay of Free Radical Scavenging Activity

Principle of Assay

The free radical form of $DPPH^\bullet$ is purple in colour and absorbs maximally at a wavelength of 515 nm. Antioxidants such as certain phenolic compounds are able to scavenge the free radicals of $DPPH^\bullet$ resulting in a decrease in intensity of the purple colour, which can be measured spectrophotometrically.

Free Radical Scavenging Assay

Stock solution of $DPPH^\bullet$ was diluted to 0.025 mg/ml with water to give a final solution in 50% methanol. Gallic acid was prepared at the concentration of 300 ppm (300 µg/ml). Substances to be tested were prepared in water to give a concentration of 300 ppm GAE.

To 975 µl of $DPPH^\bullet$ solution in a cuvette were added 25 µl of sample. Absorbance at the wavelength of 515 nm was monitored spectrophotometrically at 0.1 min intervals for 2 min. The control was treated in the same manner except that the sample was replaced with water. Blank contained 50% of methanol in place of $DPPH^\bullet$ and water in place of sample. Values for the blank were subtracted from the test values.

Concentration of $DPPH^\bullet$ at any particular absorbance was calculated from the $DPPH^\bullet$ standard curve using the formula, $$Y = aX + b$$

Where, Y=absorbance (at 515 nm)
X=concentration of $DPPH^\bullet$ (µg/mL)
a=Linear regression coefficient
b=y-intercept Since the standard curve passes through the origin, therefore b=0 Rearranging the formula, $$X = \frac{Y}{a} \qquad (3)$$

The percentage of $DPPH^\bullet$ remaining (% $DPPH^\bullet_{rem}$) was calculated using the formula, $$\% \ DPPH^\bullet_{rem} = \frac{[DPPH^\bullet]_t}{[DPPH^\bullet]_0} \times 100 \qquad (4)$$

Where, $[DPPH^\bullet]_t$ = concentration of $DPPH^\bullet$ at $t$ time (µg/ml)

$[DPPH^\bullet]_0$ = initial concentration of $DPPH^\bullet$ (µg/ml)

Percentages of $DPPH^\bullet$ remaining against time were plotted and the graph obtained was used to estimate the half-life ($t_{1/2}$), the time required to decrease by 50% the initial $DPPH^\bullet$ concentration.

Oil palm extract showed significant scavenging activity as compared with the control (ANOVA, F=74.314, p<0.001). Oil palm extracts gave $t_{1/2}$ values: 0.64 min and less. The half life of less than 0.7 min (to scavenge 50% of the initial DPPH radicals as indicated by the $t_{1/2}$ values) at this concentration of phenol suggests that phenolic compounds may exert beneficial effects in the body and skin because of their high efficacy and rapidity in scavenging free radicals.

Assay Using β-Carotene-Linoleate

Principle of Assay

Linoleic acid (polyunsaturated fatty acid) and β-carotene are sensitive to heat, light and air. Upon complete oxidation of its double bonds, β-carotene (orange in colour) becomes colourless. The degree of oxidation is reflected by the decrease in intensity of the orange colour, which can be monitored spectrophotometrically. Oxidation of β-carotene occurs spontaneously but at a much slower rate. Linoleic acid is readily oxidised in the presence of heat, air and light to the peroxide form. Free radicals (peroxyl radicals, alkoxyl radicals and hydroxyl radicals) are produced during the process of peroxide formation. Free radicals when present speed up the oxidation of β-carotene. In the presence of antioxidants, such as some phenolic compounds, the formation of the free radicals is hindered and hence will slow down the discolouration of β-carotene.

Procedure of Assay

Oil palm phenolic extract was prepared to give a concentration of 5,000 ppm GAE. Gallic acid was prepared in water at the concentration of 5,000 ppm.

Two bottles of 100 ml of water were oxygenated by aerating with compressed air (purchased from Malaysian Oxygen Berhad, Malaysia) for 5 min.

β-Carotene solution was prepared by dissolving 2.0 mg of β-carotene in 10 ml of chloroform. Two ml of this solution were pipetted into a 250 ml round-bottom flask. Chloroform was removed under vacuum, using rotavapor (model 461 purchased from Buchi Laboratoriums-Technik AG Postfach, Switzerland) and suction pump (model SUQ3 purchased from Heto Lab Equipment A/S, Denmark) at 40° C. To this round-bottom flask, 40 mg of linoleic acid, 400 mg of Tween 40 and 100 ml of aerated water were added. At the same time, a similar emulsion but without β-carotene was prepared. The flasks were shaken vigorously for a period of 5 min.

Samples of 100 µl and 200 µl were pipetted into separate test tubes. The total volume was adjusted with methanol to give a final volume of 200 µl. The control was treated in the same manner except that the sample was replaced with water. Blanks contained samples and emulsion without β-carotene. Values for the blanks were subtracted from the test values.

Absorbance of the emulsion containing β-carotene was measured spectrophotometrically at 470 nm. The value of this absorbance was treated as the zero time absorbance. Immediately after the absorbance was taken, 4.8 mL of the emulsion was added to the test tube containing the sample. The final concentrations of the phenolic compounds in the assay media were 100 and 200 ppm GAE. Subsequent absorbance measurements were taken at 30 min intervals over a 2 hr period by keeping the samples in a water bath at 50° C.

Percentage of β-carotene remaining was calculated as follows:

$$\% \text{ remaining } \frac{OD_t}{OD_0} \times 100 \quad (6)$$

Where, $OD_t$ = Absorbance at $t$ time $OD_0$ = Initial absorbance

Oil palm phenolic extract showed potent inhibition against oxidation as shown in the figure below.

Inhibition of Oxidation of β-Carotene by Various Samples.

Figure 2:
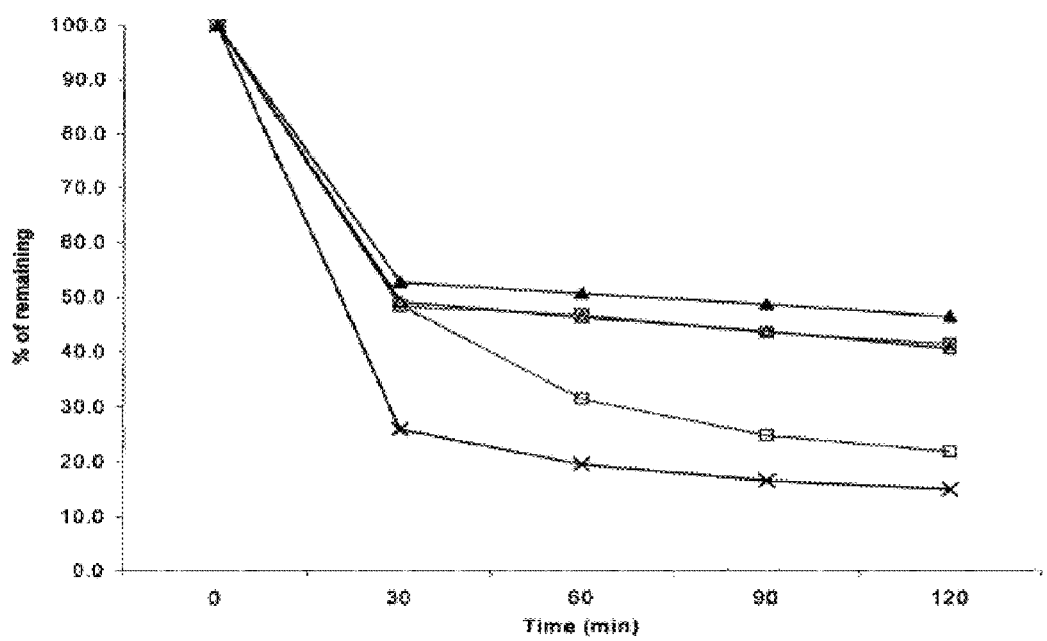
FIG. 2 is a graph of data showing inhibition against oxidation of oil palm phenolic extract, as described in "Assay using β-carotene-linoleate."

Lines in FIG. 2 show the percentages of β-carotene remaining with time for control (X - - - X), gallic acid at 100 ppm (□ - - - □), 200 ppm (■ ------ ■); and oil palm extract at 100 ppm GAE (Δ - - - Δ) and 200 ppm GAE (◄ ------ ◄).

It is understood that the composition of the present invention may be prepared in the form of cosmetics and dermatological care form, for example but not limiting to gel, solution, cream or powder, personal care products such as skin creams, lotions, skin toners, face packs, and cleansing agents; make-up cosmetics such as lipsticks and foundation; or hair cosmetics. The cosmetics may be in any form without limitation. Additionally, the skin preparation for external use may be, for example, ointment or various dermatological agents.

It should be understood that the invention as disclosed and described herein can be used not only in the respective combination as indicated but also in a singular fashion without departing from the intended scope of the present invention.

The invention claimed is:

1. A method for treating or reducing the appearance of wrinkles or fine lines on skin, the method comprising applying to the skin an effective amount of a cosmeceutical composition comprising a mixture of phenolic compounds and glycerol extracted from vegetation liquor of palm oil milling process, wherein the composition comprises an effective amount of said mixture to reduce skin ageing and/or the appearance of wrinkles or fine lines on the skin.

2. The method of claim 1, wherein the composition further comprises a fruit acid and/or fruit sugar.

3. The method of claim 1, wherein improving skin health includes inhibiting skin aging.

4. The method of claim 1, wherein the composition is rich in antioxidants.

5. The method of claim 1, wherein the composition is prepared in a form which enables direct application to the skin.

6. The method of claim 1, wherein the composition is prepared in the form of a cosmetic.

7. The method of claim 1, wherein the composition is prepared in the form of an herbal bath.

8. The method of claim 1, wherein the composition is in the form of gel.

9. The method of claim 1, wherein the composition is in the form of a powder.

10. The method of claim 1, wherein the composition is in the form of a solution or an ointment.

* * * * *